US010034096B2

(12) United States Patent
Ando

(10) Patent No.: US 10,034,096 B2
(45) Date of Patent: Jul. 24, 2018

(54) HEADPHONE

(71) Applicant: Murata Manufacturing Co., Ltd., Nagaokakyo-shi, Kyoto-fu (JP)

(72) Inventor: Masamichi Ando, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 27 days.

(21) Appl. No.: 15/069,023

(22) Filed: Mar. 14, 2016

(65) Prior Publication Data

US 2016/0198269 A1 Jul. 7, 2016

Related U.S. Application Data

(63) Continuation of application No. PCT/JP2014/074621, filed on Sep. 18, 2014.

(30) Foreign Application Priority Data

Sep. 27, 2013 (JP) ................................ 2013-202579

(51) Int. Cl.
*H04R 1/10* (2006.01)
*H04R 17/00* (2006.01)
(Continued)

(52) U.S. Cl.
CPC ......... *H04R 17/005* (2013.01); *H04R 1/1075* (2013.01); *H04R 1/1091* (2013.01);
(Continued)

(58) Field of Classification Search
CPC ...... H04R 17/005; H04R 1/1008; H04R 7/04; H04R 2203/00; H04R 1/1075;
(Continued)

(56) References Cited

U.S. PATENT DOCUMENTS 3,919,501 A * 11/1975 Cech .................... H04R 1/1066 381/377
4,278,852 A * 7/1981 Gorike ................... H04R 19/02 381/354
(Continued)

FOREIGN PATENT DOCUMENTS

EP 1147680 * 2/1999 ............ H04R 5/033
JP 6-038288 A 2/1994
(Continued)

OTHER PUBLICATIONS

Mike, "AKG K1000" [Online], Mar. 1, 2012, http://www.headfonia.com/old-champ-the-akg-k1000, all.*
(Continued)

*Primary Examiner* — Vivian Chin
*Assistant Examiner* — Ubachukwu Odunukwe
(74) *Attorney, Agent, or Firm* — Arent Fox LLP

(57) ABSTRACT

A headphone is disclosed that includes a headband and a pair of sound emitting units. The headband is a band-shaped body that is curved in an arch shape. The sound emitting units each have a flat shape and are disposed at both ends of the headband. The sound emitting units each include a piezoelectric actuator of a flat film shape disposed on a flat plane of a sound emission housing of a flat shape. The piezoelectric actuator includes a piezoelectric film made of an organic piezoelectric material such as PLLA, and first and second driving conductors disposed on opposing principal planes of the piezoelectric film.

19 Claims, 3 Drawing Sheets

(51) Int. Cl.

| | |
|---|---|
| ***H04R 5/033*** | (2006.01) |
| ***H04R 29/00*** | (2006.01) |
| *H04R 7/04* | (2006.01) |

(52) U.S. Cl.
CPC ........... *H04R 5/033* (2013.01); *H04R 29/001* (2013.01); *H04R 1/1008* (2013.01); *H04R 1/1041* (2013.01); *H04R 1/1058* (2013.01); *H04R 7/04* (2013.01); *H04R 2203/00* (2013.01)

(58) Field of Classification Search
CPC .... H04R 29/001; H04R 1/1091; H04R 5/033; H04R 1/1041; H04R 1/10; H04R 1/1058; H04R 5/02
USPC ............................... 381/59, 190, 381, 74, 58
See application file for complete search history.

(56) References Cited

U.S. PATENT DOCUMENTS

| | | | | |
|---|---|---|---|---|
| 4,389,542 | A * | 6/1983 | Gorike .................. | H04R 1/225 381/347 |
| 5,265,165 | A * | 11/1993 | Rauch ..................... | A61F 9/045 2/10 |
| 5,761,314 | A | 6/1998 | Inanaga et al. | |
| 6,856,073 | B2 * | 2/2005 | Bryant .................. | F04B 43/095 310/324 |
| 2003/0059078 | A1 * | 3/2003 | Downs, Jr. ............. | H04R 1/083 381/381 |
| 2007/0129776 | A1 * | 6/2007 | Robins ................. | A61N 5/0613 607/88 |
| 2010/0020252 | A1 | 1/2010 | Otsuki et al. | |

FOREIGN PATENT DOCUMENTS

| | | | |
|---|---|---|---|
| JP | 11-308666 | A | 11/1999 |
| JP | 2002536699 | A | 10/2002 |
| JP | 2005318087 | A | 11/2005 |
| JP | 2007019957 | A | 1/2007 |
| JP | 2008131439 | A | 6/2008 |
| JP | 2010213099 | A | 9/2010 |
| WO | WO 1995/020866 | A1 | 8/1995 |

OTHER PUBLICATIONS

Headfonia, AKG K1000 Review Headfonia Headphone Reviews, Mar. 1, 2012, all pages pertinent.*
International Search Report for PCT/JP2014/074621, dated Dec. 22, 2014.
Written Opinion for PCT/JP2014/074621, dated Dec. 22, 2014.
Mike, "Old Champ:The AKG K1000" Online, Jan. 3, 2012, Internet URL http://www.headfonia.com/old-champ-the-akg-k1000/.
"AKG K1000" [online], May 20, 2006, retrieved Mar. 28, 2018, Internet <URL: http://www.geocities.jp/mister_terch/AKGK1000.html>.
International Search Report issued for PCT/JP2014/074621, dated Dec. 22, 2014.
Written Opinion of the International Searching Authority issued for PCT/JP2014/074621, dated Dec. 22, 2014.

* cited by examiner

HEADPHONE

CROSS REFERENCE TO RELATED APPLICATIONS

The present application is a continuation of PCT/JP2014/074621 filed Sep. 18, 2014, which claims priority to JP Application No. 2013-202579, filed Sep. 27, 2013, the entire contents of each of which are incorporated herein by reference.

TECHNICAL FIELD

The present invention relates to a headphone that includes a speaker unit that includes a piezoelectric element.

BACKGROUND

Conventionally, various headphones are devised and are practically used. Among these headphones, a headphone for which a piezoelectric body is used as disclosed in Patent Literature 1 is also devised.

The headphone disclosed in Patent Literature 1 includes a band that allows the headphone to be attached to a head, and a speaker unit attached to both ends of the band and equipped with ear pads. In sound emission housing, speakers for which a piezoelectric ceramics plate is used are attached. By driving this piezoelectric ceramics plate according to a sound emission drive signal, sounds are emitted to eardrums of a user. Further, the speaker unit including the piezoelectric ceramics plate provides sounds to a user by way of bone conduction, too, by placing the headphone disclosed in Patent Literature 1 in contact with a bone via a user's skin.

PTL 1: Japanese Patent Application Laid-Open No. 2007-19957.

However, the headphone of Patent Literature 1 needs to cause sound emission and bone conduction vibration with respect to the eardrums by using one piezoelectric ceramics plate. Therefore, the piezoelectric ceramics plate becomes larger and heavier.

Further, when a shape of the piezoelectric ceramics plate becomes larger, the piezoelectric ceramics plate likely cracks upon vibration.

Furthermore, the headphone of Patent Literature 1 has a thick shape of the speaker unit since the ear pads of the speaker unit are filled with a fluid. Hence, even when the piezoelectric ceramics plate, which is supposed to be able to form the thin speaker unit is used, the speaker unit eventually becomes thick and large.

SUMMARY OF THE INVENTION

Therefore, the present disclosure provides a headphone that is thin and light and has good sound characteristics.

The present invention relates to a headphone that includes a headband of an arch shape, and a sound emission housing attached to both ends of the headband. Moreover, the sound emission housing has a flat shape and, a piezoelectric actuator of a flat film shape including an organic piezoelectric film with a driving conductor attached to the sound emission housing.

According to this configuration, the vibration of the piezoelectric actuator vibrates the flat shaped sound emission housing to emit sounds having strong directivity in a direction orthogonal to a flat plane. When the headband is attached to a user's head, the direction with strong directivity is the direction of the user's ears, and therefore the emitted sounds are effectively transmitted to the user's ears. Further, an organic piezoelectric film is used, making it possible to configure a thin and light headphone.

Furthermore, preferably, the headphone according to the present invention further includes a spacer member at a specific position on an inner circumferential surface of the headband and between a center and both ends in a direction in which the arch shape extends.

According to this configuration, the spacer member comes into contact with the user's head, making it possible to move the sound emission housing away from the ears. Consequently, the user can listen to sounds from outside while listening to sounds emitted by the headphone.

Further, preferably, in the headphone according to the present invention, a piezoelectric sensor of a flat film shape including an organic piezoelectric film and a detection conductor is attached to the headband.

According to this configuration, the piezoelectric sensor can receive an input of an operation.

Further, preferably, in the headphone according to the present invention, at least one layer of the organic piezoelectric film is made of polylactic acid or polyvinylidene fluoride.

According to this configuration, it is possible to provide a speaker that is thin and has high piezoelectric conversion efficiency.

Further, in the headphone according to the present invention, the sound emission housing is made of an insulation material having translucency, and the driving conductor is made of a conductive material having translucency.

According to this configuration, it is possible to make portions of the headphone facing the user's ears transparent.

Further, in the headphone according to the present invention, the headband, the sound emission housing and the spacer member are made of an insulation material having translucency, and the piezoelectric actuator is made of a material having translucency.

Furthermore, in the headphone according to the present invention, the headband and the sound emission housing are made of an insulation material having translucency, and the piezoelectric actuator and the piezoelectric sensor are made of a material having translucency.

According to these configurations, it is possible to make the entire headphone transparent. That is, it is possible to make the user look like as if the user did not put on the headphone. Alternatively, it is possible to make the user look stylish.

Further, preferably, in the headphone according to the present invention, the headband and the sound emission housing are integrally molded.

This configuration does not adopt a structure that the headband and the sound emission housing are connected by an adhesive or a connection mechanism. Consequently, it is possible to increase the strength of the entire headphone. Further, it is possible to make an appearance beautiful.

According to the present invention, it is possible to realize a headphone which is thin and light and has good sound characteristics.

DETAILED DESCRIPTION

Figure 1:
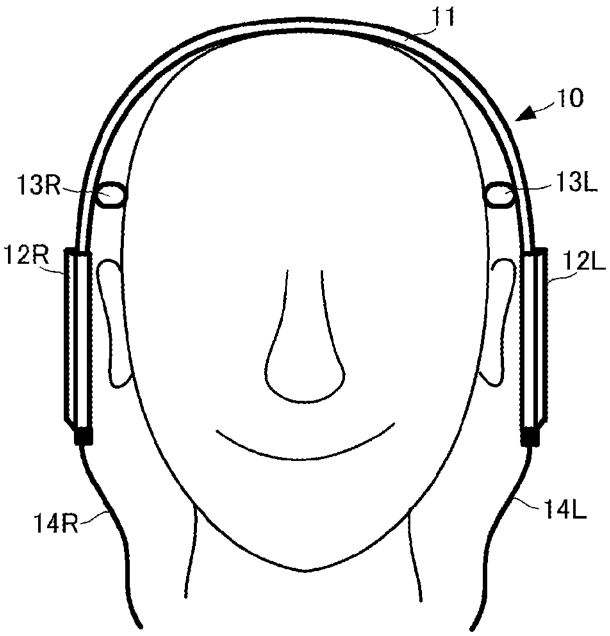
FIG. 1 is a front view of a headphone according to a first embodiment of the present invention.
Figure 2:
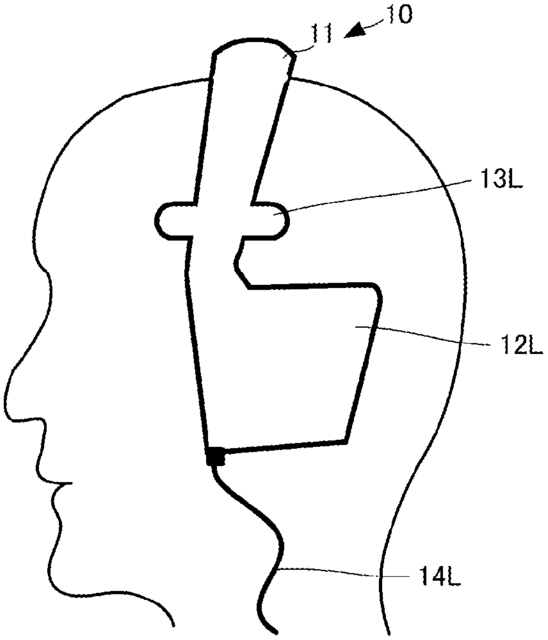
FIG. 2 is a left side view of the headphone according to the first embodiment of the present invention.

A headphone according to a first embodiment of the present invention will be described with reference to the drawings. FIG. 1 is a front view of the headphone according to the first embodiment of the present invention. FIG. 2 is a left side view of the headphone according to the first embodiment of the present invention.

A headphone 10 includes a headband 11, sound emitting units 12L and 12R and spacers 13L and 13R. A material of the headband 11 is polymer. For example, polycarbonate (PC) resin, acrylic (PMMA) resin, polyethylene terephthalate (PET) resin, ABS resin, polyvinyl chloride (PVC) resin and the like can be used for the headband 11. In this regard, the headband 11 is preferably transparent or semi-transparent.

The headband 11 is a band-shaped body of an arch shape seen from a front view. In other words, the headband 11 is formed in an elongated shape and has a shape that is curved along an elongation direction.

The sound emitting units 12L and 12R each have a flat shape. The sound emitting unit 12L is coupled to one end of the headband 11 in the overlapping direction, and the sound emitting unit 12R is connected to another end of the headband 11 in the elongation direction. Flat planes of the sound emitting units 12L and 12R are vibration planes of the sound emitting units 12L and 12R.

The sound emitting units 12L and 12R are disposed such that the flat planes face each other or substantially face each other. In this regard, preferably, an interval between front surface side end portions of the sound emitting units 12L and 12R is substantially the same as that of back surface side end portions. More preferably, the interval between the front surface side end portions of the sound emitting units 12L and 12R is narrower than that of the back surface side end portions. According to an aspect where the interval between the front surface side end portions of the sound emitting units 12L and 12R is narrower than the interval between the back surface side end portions, it is possible to form vibration planes that are configured along shapes of ears of a person. Consequently, it is possible to more effectively emit sounds to the ears (eardrums).

Figure 3A:
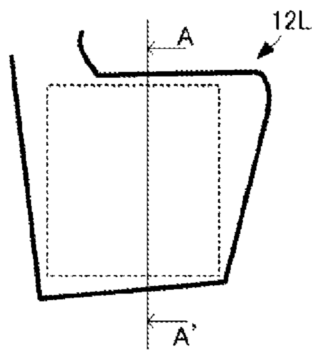
FIGS. 3(A) and 3(B) are a view illustrating a configuration of a sound emitting unit of the headphone according to the first embodiment of the present invention.
Figure 3B:
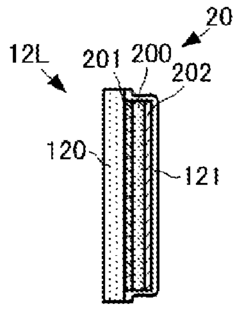

The sound emitting units 12L and 12R each include a sound emission housing 120, a piezoelectric actuator 20 and a protection film 121. FIG. 3(A) is a view illustrating a configuration of sound emitting units of the headphone according to the first embodiment of the present invention, with FIG. 3(A) specifically illustrating the headphone seen from a left side view and FIG. 3(B) is an A-A' sectional view in FIG. 3(A). In addition, the sound emitting unit 12L will be described with reference to FIGS. 3(A) and 3(B) as an example. However, the sound emitting unit 12R also adopts the same structure. Hereinafter, only the sound emitting unit 12L will be described.

According to the exemplary embodiment, each sound emission housing 120 is made of insulation resin of a flat shape. Each sound emission housing 120 may be made of a material different from or the same material as that of the headband 11. When the materials of each sound emission housing 120 and the headband 11 are the same, each sound emission housing 120 is desirably molded with the headband 11.

The piezoelectric actuator 20 is formed in a flat film shape and is attached to the flat plane of the sound emission housing 120. In this regard, the piezoelectric actuator 20 is attached such that the flat film plane of the piezoelectric actuator 20 is parallel to the flat plane of the sound emission housing 120. The piezoelectric actuator 20 is attached using, for example, an adhesive. In addition, the piezoelectric actuator 20 may be attached to a plane at an inner circumference side of the sound emission housing 120 or may be attached to a plane of an outer circumference side. On the plane of the sound emission housing 120 to which the piezoelectric actuator 20 is attached, the protection film 121 is formed in a shape that covers the piezoelectric actuator 20. Preferably, the protection film 121 is made of an insulation material. For example, the protection film 121 is made of a PET film. This protection film 121 is provided, so that it is possible to protect the piezoelectric actuator 20 from external environment. Further, it is possible to electrically insulate the piezoelectric actuator 20 from the external environment.

The piezoelectric actuator 20 includes a piezoelectric film 200, a first driving conductor 201 and a second driving conductor 202. The first driving conductor 201 is formed on one principal plane (flat film plane) of the piezoelectric film 200, and the second driving conductor 202 is formed on the other principal plane (flat film plane) of the piezoelectric film 200.

The piezoelectric film 200 includes polylactic acid (abbreviated as PLLA below) or polyvinylidene fluoride (abbreviated as PVDF below) as a material. In addition, the material of the organic piezoelectric film 200 is not limited to the PLLA and the PVDF. For the organic piezoelectric film 200, a piezoelectric resin film such as a material including polyurea and a piezoelectric resin film of a group having a high piezoelectric constant can be used. When PLLA is used for the organic piezoelectric film 200, the organic piezoelectric film 200 may be formed in a rectangular shape by cutting the organic piezoelectric film 200, such that each outer circumference side is formed nearly 45° with respect to an extension direction.

For the first and second driving conductors 201 and 202, materials whose main components are indium tin oxide (ITO), IZO (registered trademark), zinc oxide (ZnO), polythiophene and polyaniline can be used according to an exemplary embodiment. Further, for the first and second driving conductors 201 and 202, silver nanowires, carbon nanotubes, graphen and the like can be used. Furthermore, when the first and second driving conductors 201 and 202 do not need to have translucency, it is also possible to use deposited aluminum electrodes according to another embodiment. The first and second driving conductors 201 and 202 are connected to signal cables 14L and 14R, and sound emission drive signals are applied to the first and second driving conductors 201 and 202 via the signal cables 14L and 14R.

According to the exemplary embodiment, the piezoelectric actuator 20 is structurally configured to extend and contract along a direction parallel to the flat plane by applying signals to the first and second driving conductors 201 and 202. With the extension and the contraction of this piezoelectric actuator 20, a stress is applied to the sound emission housing 120 of the flat shape, and the sound emission housing 120 vibrates in a direction orthogonal to the flat plane. That is, the sound emission housing 120 functions as a diaphragm and emits a sound. Thus, a sound having strong directivity in a direction orthogonal to the flat plane of the sound emission housing 120, i.e., the flat planes of the sound emitting units 12L and 12R is produced.

The spacers 13L and 13R are formed in nearly columnar shapes or elliptical shapes, and are coupled to the headband 11 such that a longitudinal direction of the spacers 13L and 13R matches with a width direction of the headband 11. According to the exemplary embodiment, the spacer 13L is coupled to a halfway position between a center and one end of the headband 11 in the elongation direction (extending direction). Moreover, the spacer 13R is coupled to a halfway position between a center and the other end of the headband 11 in the elongation direction (extending direction). The spacers 13L and 13R are coupled to a curving inside of the headband 11. In addition, the spacers 13L and 13R are not coupled so as to allow the user to change coupling positions, and the user may optionally couple the spacers 13L and 13R to the headband 11 later. The spacers 13L and 13R are preferably made of a soft material such as silicone or urethane.

The configuration described above provides a thin and light headphone. Further, each component can be made of a material having translucency, so that it is possible to realize a transparent headphone. Consequently, it is possible to realize a stylish headphone which looks like as if the user did not put on the headphone.

The headphone 10 employing such a configuration is attached to a user's head and used as illustrated in FIGS. 1 and 2. More specifically, the headphone 10 is attached to the user's head such that the headband 11 is arranged along a shape of the head, and the sound emitting units 12L and 12R are arranged at positions facing the user's ears.

In a state where the headphone 10 is not attached to the head, i.e., in a state where the headphone 10 does not receive an external stress, the headphone 10 has such a shape that a curve of the headband 11 is tight and the sound emitting units 12L and 12R are narrower than a width of a user's face. However, when the above-described material is used for the headband 11, the headband 11 has elasticity. When, for example, the user widens the both ends at sides of the sound emitting units 12L and 12R, the headphone 10 can be attached to the user's head in a state where a stress is applied to a side of the user's head.

In this regard, when the spacers 13L and 13R are placed in contact with the user's head, it is possible to prevent the sound emitting units 12L and 12R from directly contacting the ears. That is, by optionally setting the shapes of the spacers 13L and 13R, it is possible to place the sound emitting units 12L and 12R close to each other without placing the sound emitting units 12L and 12R in contact with the ears. According to this configuration, it is possible to prevent the ears from aching even when the headphone 10 is attached to the user's head for a long period of time. Further, the ears are not closed by the sound emitting units 12L and 12R, so that it is possible to hear external environment sounds while listening to sounds from the headphone 10.

Furthermore, the sound emitting units 12L and 12R for which the piezoelectric actuators 20 of the flat film shapes are used provide lower absolute sound pressures than those of conventional sound emitting units for which electromagnetic coils are used. However, according to the configuration of the present embodiment, the sound emitting units 12L and 12R are near the ears, so that the sound volumes the ears feel can reach sufficiently practical sound pressure levels.

Further, the sound emitting units 12L and 12R for which the piezoelectric actuators 20 of the flat film shapes are used emit sounds not only to the inner circumference side of the headphone 10 but also to the outer circumference side, and, in a low sound range, a sound at the inner circumference side and a sound at the outer circumference side weaken each other. However, a wavelength is long in the low sound range, and the sound emitting units 12L and 12R are near the ears, so that sounds in the low sound range hardly functions to weaken each other. Consequently, even when the sound emitting units 12L and 12R for which the piezoelectric actuators 20 are used are used for the headphone 10, it is possible to obtain a sufficiently practical sound pressure level in a low sound range.

Thus, by using the configuration according to the present embodiment, it is possible to realize a headphone which is thin and light and has good sound quality characteristics.

Particularly, the headphone 10 employing such a configuration is more suitable in an aspect for use in indoor environment than in outdoor environment. For example, the headphone 10 is more suitable in an aspect for use by way of connection with a personal computer, a tablet terminal device or a smartphone.

In such environment, it is possible to listen to other sounds from indoor such as a chime, an indoor telephone and a conversation of other people while listening to sounds from the headphone 10.

Further, the headphone 10 employing such a configuration is more suitable for use in a long period of time. As described above, the sound emitting units 12L and 12R of the headphone 10 according to the present embodiment do not directly contact ears. Consequently, the ears do not ache, and ear canals do not become stuffy. Consequently, long-term use does not cause discomfort.

In addition, an example where one piezoelectric film is used for each piezoelectric actuator 20 according to the present embodiment has been described. However, a plurality of piezoelectric films may be laminated. According to this configuration, it is possible to increase an extension and contraction amount with respect to a drive voltage, and improve actuation characteristics. Consequently, it is possible to emit sufficiently practical sound pressures by a sound emission drive signal of a lower drive voltage.

Figure 4A:
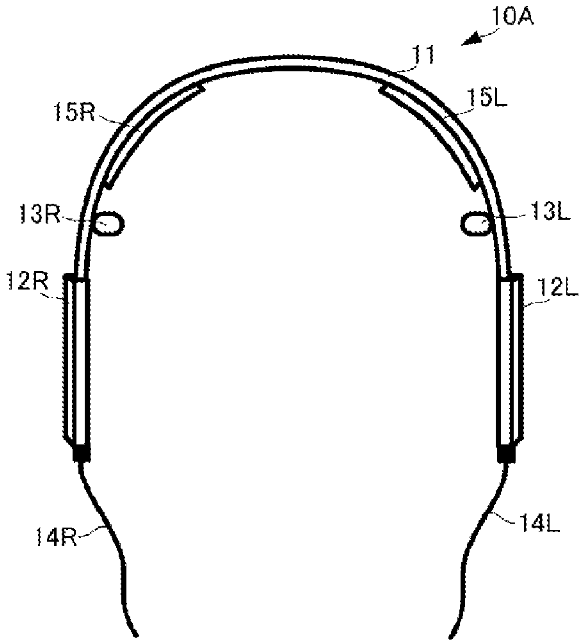
FIGS. 4(A) and 4(B) are front view and a left side view of the headphone according to a second embodiment of the present invention.
Figure 4B:
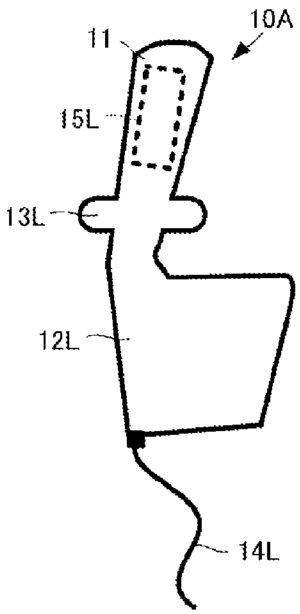

Next, a headphone according to a second embodiment of the present invention will be described with reference to the drawings. FIG. 4(A) is a front view of the headphone according to the second embodiment of the present invention, and FIG. 4(B) is a left side view of the headphone according to the second embodiment of the present invention.

A headphone 10A according to the present embodiment differs from a headphone 10 according to the first embodiment in additionally including piezoelectric sensors 15L and 15R, and other components are the same as those of the headphone 10 described in the first embodiment. Hence, only differences from the headphone 10 described in the first embodiment will be more specifically described.

Each basic structure of the piezoelectric sensors 15L and 15R is the same as that of a piezoelectric actuator 20. That is, the piezoelectric sensors 15L and 15R each include detection conductors on both principal surfaces of a piezoelectric film.

The piezoelectric sensor 15L is attached between a center and one end of a headband 11 along an extending direction. More preferably, the piezoelectric sensor 15L is attached between a center of the headband 11 along the extending direction, and an attachment position of a spacer 13L.

The piezoelectric sensor 15R is attached between a center and the other end of the headband 11 along the extending direction. More preferably, the piezoelectric sensor 15R is attached between a center of the headband 11 along the extending direction, and an attachment position of a spacer 13R.

The piezoelectric sensors 15L and 15R are attached to a plane at an inner circumference side of the headband 11. On the plane at the inner circumference side of the headband 11, a protection film having an insulation property is formed to cover the piezoelectric sensors 15L and 15R.

The piezoelectric sensors 15L and 15R are connected to a press detection circuit (not illustrated) via detection wirings (not illustrated). The detection wirings are formed on, for example, the headband 11, sound emitting units 12L and 12R and signal cables 14L and 14R. The press detection circuit is provided to, for example, a device which produces a sound emission drive signal.

By employing such a configuration, when a pressing force is applied to the headband 11 and the headband 11 is deformed, the piezoelectric films of the piezoelectric sensors 15L and 15R are displaced in response to this deformation of the headband 11. The detection conductor detects electric charges produced by this displacement, so that it is possible to detect a press of the headband. A command corresponding to a detection signal of the pressing force is stored in the press detection circuit, and the press detection circuit determines a command based on the detection signal and gives a sound drive signal to a sound emission control unit which produces a sound emission drive signal. The sound emission control unit changes a signal level of the sound emission drive signal according to this command, or controls generation and stop of the sound emission drive signal.

Thus, by using the configuration according to the present embodiment, and only by applying a pressing force to the headband 11, it is possible to control sound emission. Consequently, it is possible to control sound emission by an easy operation. It is possible to perform sound emission control of raising a signal level of a sound emission drive signal by pushing a left surface side of the headband 11, and lowering the signal level of the sound emission drive signal by pushing a right surface side of the headband 11.

In this regard, when the left surface side of the headband 11 is pushed, not only the piezoelectric sensor 15L, but also the piezoelectric sensor 15R, produce electric charges. However, when the left surface side of the headband 11 is pushed, a produced electric charge amount of the piezoelectric sensor 15L is larger than a produced electric charge amount of the piezoelectric sensor 15R. Therefore, the press detection circuit compares these produced electric charge amounts and selects a larger produced electric charge amount and, consequently, can detect a command accurately.

An actual operation may be an operation of applying a press or an operation of tapping the headband 11. A signal upon a press and a signal upon a tap produce different waveforms, and a difference between these waveforms may be recognized and different operations may be allocated to the press and the tap. When, for example, the right side of the headband 11 is tapped, music is turned on or off, and, when the left side is tapped, music is selected. Further, when the right side is pressed, a sound volume is increased and, when the left side is pressed, a sound volume is decreased.

Thus, by using the configuration according to the present embodiment, a headphone is provided that is thin and light and has good sound quality characteristics and which can receive an input of an operation.

In addition, instead of the piezoelectric sensors 15L and 15R, capacitive touch detection sensors may be used. In this case, by using the capacitive position detection sensors which can detect one-dimensional positions, it is possible to accept signal level control of a sound emission drive signal depending on an operation detection direction.

Further, both of the piezoelectric sensors 15L and 15R and the capacitive position detection sensors may be used. In this case, the piezoelectric sensors 15L and 15R and the capacitive position detection sensors may be disposed at different positions or may be laminated and disposed. Consequently, it is possible to receive more various operation inputs.

For example, the press detection circuit of the piezoelectric sensors 15L and 15R can receive wake-up or on/off of an operation input, and the capacitive position detection sensors can receive a specific operation with respect to a signal level of a sound emission drive signal. In this example, even when the headband 11 is unintentionally touched, signal level control is not performed on a sound emission drive signal. Further, only when the headband 11 is intentionally touched, it is possible to perform signal level control on a sound emission drive signal. In this regard, at a point of time at which an operation input can be received, the sound emitting units 12L and 12R can also emit sounds indicating that an operation can be accepted.

In addition, in each of the above embodiments, spacers 13L and 13R are provided. However, the spacers 13L and 13R can also be omitted.

Figure 5:
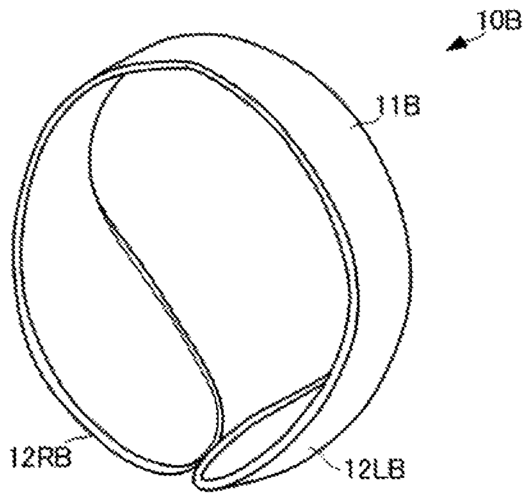
FIG. 5 is an external appearance perspective view of the headphone according to another aspect of an embodiment of the present invention.

Further, in each of the above embodiments, a case where each shape of the sound emitting units 12L and 12R seen from a plan view (each shape of the headphones 10 and 10A seen from a side view) is nearly rectangular has been described. However, each shape is not limited to this. For example, the shape may have a shape illustrated in FIG. 5. FIG. 5 is an external appearance perspective view illustrating a headphone according to another aspect of the embodiment of the present invention.

In a headphone 10B, a headband 11B and sound emitting units 12LB and 12RB (more accurately, sound emission housings 120 of the sound emitting units 12LB and 12RB) are integrally molded. The sound emitting units 12LB and 12RB each include a piezoelectric actuator of a flat film which is not illustrated. The sound emitting units 12LB and 12RB each have a shape formed by cutting part of a sphere, and have a shape which bulges outward. The sound emitting units 12LB and 12RB each have such a shape, so that it is possible to softly cover ears without sealing the ears. In this case, spacers may not be used.

Further, a disconnection detecting unit may be added to the headphone according to each of the embodiments. The disconnection detecting unit may be configured together with the above sound emission control unit and the press detection circuit. The disconnection detecting unit is connected to a piezoelectric actuator 20 via signal cables 14L and 14R. The disconnection detecting unit gives a disconnection detection signal of a higher frequency wave than an audible range, to the piezoelectric actuator 20 via the signal cables 14L and 14R, and observes a disconnection detection signal. When the signal cables 14L and 14R or connection portions of the signal cables 14L and 14R and the actuators 20 are disconnected, the disconnection detecting unit can detect that a disconnection detection signal does not flow to a closed circuit formed by the signal cables 14L and 14R and the piezoelectric actuator 20. By detecting that the disconnection detection signal does not flow, the disconnection detecting unit can detect disconnection, and the sound emission control unit can stop the sound emission drive signal. In this case, the disconnection detection signal is a signal of a higher frequency wave than the audible range, so that each piezoelectric actuator 20 functions simply as a capacitor for the disconnection detection signal. Consequently, a sound is hardly produced by the disconnection detection signal, so that the user does not feel uncomfortable. In addition, a case where only disconnection is detected has been described. However, by taking advantage of that feature, each piezoelectric actuator can function as a capacitor for a disconnection detection signal. It is also possible to measure an impedance of the closed circuit and detect an abnormality of each piezoelectric actuator based on a change in the impedance.

Further, an example where the thickness of the sound emission housing 120 is fixed has been described in each of the above embodiment. However, the thickness may be partially differed by making thin a range of a portion at which each piezoelectric actuator 20 is attached. For example, thicknesses at both ends in a direction in which each piezoelectric actuator 20 extends may be made thick, and thicknesses of other portions may be made thin. Consequently, it is possible to cause each sound emission housing 120 to more effectively vibrate.

DESCRIPTION OF REFERENCE SYMBOLS

10,10A,10B: HEADPHONE
11,11B: HEADBAND
12L,12R,12LB,12RB: SOUND EMITTING UNIT
13L,13R: SPACER
14L,14R: SIGNAL CABLE
15L,15R: PIEZOELECTRIC SENSOR
20: PIEZOELECTRIC ACTUATOR
120: SOUND EMISSION HOUSING
121: PROTECTION FILM
200: PIEZOELECTRIC FILM
201: FIRST DRIVING CONDUCTOR
202: SECOND DRIVING CONDUCTOR

The invention claimed is:

1. A headphone comprising:

a headband having an arch shape;

a first sound emitting unit coupled to the headband and comprising a first flat sound emission housing lying in a first plane and a first flat piezoelectric actuator lying in a second plane, the first sound emission housing being adhesively coupled to the first piezoelectric actuator such that the first and second planes are parallel;

a second sound emitting unit coupled to the headband and comprising a second flat sound emission housing lying in a third plane and a second flat piezoelectric actuator lying in a fourth plane, the second sound emission housing being adhesively coupled to the second piezoelectric actuator such that the third and fourth planes are parallel;

the first piezoelectric actuator being structurally configured to extend and contract in a direction parallel to the second plane when a first audio driving signal is applied thereto and causing the first sound emission housing to vibrate in a direction orthogonal to the first plane;

the second piezoelectric actuator being structurally configured to extend and contract in a direction parallel to the fourth plane when a second audio driving signal is applied thereto and causing the second sound emission housing to vibrate in a direction orthogonal to the third plane; and an audio source which:

supplies the first audio drive signal to the first piezoelectric actuator;

supplies the second audio drive signal to the second piezoelectric actuator;

supplies a third audio drive signal having a frequency higher than the audible range to the first piezoelectric actuator;

supplies a fourth audio drive signal having a frequency higher than the audible range to the second piezoelectric actuator; and stops supplying the first and second audio drive signals to the first and second piezoelectric actuators when the audio source determines that the third and/or fourth audio drive signals are no longer being received by the first and second piezoelectric actuators, respectively.

2. The headphone according to claim 1, wherein the headband has first and second ends and further comprises first and second spacer members disposed on an inner circumferential surface of the headband, the first spacer member being located between a center of the headband and the first end of the headband, the second spacer member being located between the center of the headband and the second end of the headband.

3. The headphone according to claim 2, wherein the headband, the sound emission housings, the piezoelectric actuators and the spacer members each comprise a translucent material.

4. The headphone according to claim 2, wherein the headband, the sound emission housings, the piezoelectric actuators and the piezoelectric sensors are each comprise a translucent material.

5. The headphone according to claim 1, further comprising at least one piezoelectric sensor having a flat film shape and including an organic piezoelectric film and a detection conductor, the piezoelectric sensor being physically coupled to the headband and sending a command signal to the audio source in response to an external mechanical force applied to the piezoelectric sensor.

6. The headphone according to claim 5, wherein the audio source modifies the first and/or second audio drive signals as a function of the command signal.

7. The headphone of claim 6, wherein the audio source modifies the first and/or second drives signals as a function of the command signal by increasing or decreasing the volume of the first and/or second drive signals.

8. The headphone of claim 6, wherein the audio source modifies the first and/or second drives signals as a function of the command signal by turning the first and/or second drive signals on and off.

9. The headphone according to claim 1, wherein each of the piezoelectric actuators comprises an organic piezoelectric film and at least one layer of the organic piezoelectric film comprises polylactic acid.

10. The headphone according to claim 1, wherein each of the piezoelectric actuators comprises an organic piezoelectric film and at least one layer of the organic piezoelectric film comprises polyvinylidene fluoride.

11. The headphone according to claim 1, wherein:

each of the sound emission housings each comprise a translucent insulation material; and each of the piezoelectric actuators comprises a respective translucent driving conductor.

12. The headphone according to claim 1, wherein the headband and the pair of sound emission housings are integrally molded with one another.

13. The headphone according to claim 1, wherein each of the piezoelectric actuators comprises a respective organic piezoelectric film surrounded by a respective pair of driving conductors.

14. A headphone comprising:

a headband having an arch shape and first and second ends;

a first sound emitting unit coupled to the first end of the headband and comprising a first flat sound emission housing lying in a first plane and a first flat piezoelectric actuator lying in a second plane, the first sound emission housing being adhesively coupled to the first piezoelectric actuator such that the first and second planes are parallel;

a second sound emitting unit coupled to the second end of the headband and comprising a second flat sound emission housing lying in a third plane and a second flat piezoelectric actuator lying in a fourth plane, the second sound emission housing being adhesively coupled to the second piezoelectric actuator such that the third and fourth planes are parallel;

the first piezoelectric actuator being structurally configured to extend and contract in a direction parallel to the second plane when a first audio driving signal is applied thereto;

the second piezoelectric actuator being structurally configured to extend and contract in a direction parallel to the fourth plane when a second audio driving signal is applied thereto; and an audio source which:

supplies the first audio drive signal to the first piezoelectric actuator;

supplies the second audio drive signal to the second piezoelectric actuator;

supplies a third audio drive signal having a frequency higher than the audible range to the first piezoelectric actuator;

supplies a fourth audio drive signal having a frequency higher than the audible range to the second piezoelectric actuator; and stops supplying the first and second audio drive signals to the first and second piezoelectric actuators when the audio source determines that the third and/or fourth audio drive signals are no longer being received by the first and second piezoelectric actuators, respectively.

15. The headphone according to claim 14, wherein the headband has first and second ends and further comprises first and second spacer members disposed on an inner circumferential surface of the headband, the first spacer member being located between a center of the headband and the first end of the headband, the second spacer member being located between the center of the headband and the second end of the headband.

16. The headphone according to claim 15, wherein the headband, the sound emitting units, the piezoelectric actuators and the spacer members each comprise a translucent insulation material.

17. The headphone according to claim 15, wherein:

the headband and the sound emitting units each comprises a translucent insulation material, and each of the piezoelectric actuators and the piezoelectric sensor comprise a translucent material.

18. The headphone according to claim 14, wherein each of the piezoelectric actuators comprises an organic piezoelectric film and at least one layer of the organic piezoelectric film comprises at least one of polylactic acid and polyvinylidene fluoride.

19. The headphone according to claim 14, wherein each of the sound emission housings and each of the drive conductors comprises a translucent insulation material.

* * * * *